United States Patent
Böhling et al.

(10) Patent No.: US 7,057,075 B2
(45) Date of Patent: Jun. 6, 2006

(54) METHOD FOR PRODUCING AMINES BY MEANS OF OLEFIN ANIMATION IN THE PRESENCE OF UNSTATURATED NITROGEN COMPOUNDS

(75) Inventors: Ralf Böhling, Griesheim (DE); Ulrich Steinbrenner, Neustadt (DE); Frank Funke, Mannheim (DE); Reinhard Dier, Freisen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 71 days.

(21) Appl. No.: 10/495,357

(22) PCT Filed: Nov. 11, 2002

(86) PCT No.: PCT/EP02/12582

§ 371 (c)(1),
(2), (4) Date: May 11, 2004

(87) PCT Pub. No.: WO03/042156

PCT Pub. Date: May 22, 2003

(65) Prior Publication Data

US 2004/0254399 A1    Dec. 16, 2004

(30) Foreign Application Priority Data

Nov. 12, 2001  (DE) ................. 101 55 523

(51) Int. Cl.
*C07C 209/60* (2006.01)
(52) U.S. Cl. .................................... 564/485
(58) Field of Classification Search ................. 564/485
See application file for complete search history.

(56) References Cited

U.S. PATENT DOCUMENTS

| | | | |
|---|---|---|---|
| 2,501,556 | A | 3/1950 | Whitman |
| 2,984,687 | A | 5/1961 | Esmay et al. |
| 3,513,200 | A | 5/1970 | Biale et al. |
| 4,186,148 | A | 1/1980 | Murata et al. |
| 4,533,751 | A | 8/1985 | Cherney et al. |
| 6,576,796 | B1 | 6/2003 | Funke et al. |
| 2001/0047097 | A1 | 11/2001 | Trauthwein et al. |

FOREIGN PATENT DOCUMENTS

| | | |
|---|---|---|
| DE | 1 034 643 | 7/1958 |
| DE | 2 161 750 | 6/1973 |
| DE | 100 41676 | 3/2002 |
| DE | 100 46608 | 3/2002 |
| EP | 1 157 983 | 11/2001 |

OTHER PUBLICATIONS

Database CAPLUS on STN, Motoyama et al., JP 54024836 (1979) (abstract).*
Howk et al., J. Am. Chem. Soc. 76 (1954) 1899 ff to 1902.
53135912 Japan (English Abstract) (1978).
54024836 Japan (English Abstract) (1979).
Derwent Abst. 377-44U—DE2161 750 (1973).
Derwent Abst. 2002-395635—DE 100 466608 (2002).

* cited by examiner

*Primary Examiner*—Brian Davis
(74) *Attorney, Agent, or Firm*—Novak Druce & Quigg, LLP; Jason D. Voight

(57) ABSTRACT

In a process for preparing alkylamines (product amines) by reacting alkenes with amines (starting amines) in the presence of a metal hydride or metal as catalyst is carried out in the process of the present invention, the reaction is carried out in the presence of a cocatalyst whose acidity is higher than that of the starting amine.

15 Claims, No Drawings

METHOD FOR PRODUCING AMINES BY MEANS OF OLEFIN ANIMATION IN THE PRESENCE OF UNSTATURATED NITROGEN COMPOUNDS

The present invention relates to a process for preparing alkylamines by reacting alkenes with amines in the presence of a metal hydride or metal as catalyst.

Amines as a group are of great importance both in nature and in the chemical industry. The amines of great industrial importance are frequently simple aliphatic compounds which are required in very large quantities for many industrial applications. Examples are further processing of the amines to produce pharmaceuticals, crop protection agents, dyes and plastics and also their use as auxiliaries in the rubber, textile and paper industries. Simple, flexible and, in particular, inexpensive methods of preparing amines are therefore of tremendous importance for many fields of organic chemistry, i.e. both for the laboratory synthesis of naturally occurring compounds or biologically active substances and for the industrial production of amines.

Classical methods of preparing amines, both in the laboratory and in industrial production, are the conversion of alcohols or alkyl halides into amines, the reductive amination of carbonyl compounds, the reduction of nitriles or azides, Michael addition of amines or ammonia onto activated alkenes and the Ritter reactions. All the methods listed use starting materials which have already been relatively highly processed, are sometimes difficult to obtain or handle and are therefore usually expensive.

These synthetic routes could be drastically shortened if an effective, generally applicable hydroamination process for alkenes were to be developed. Some processes for the hydroamination of alkenes are already known.

U.S. Pat. No. 2,501,556 and B. W. Howk et al., J. Am. Chem. Soc. 76 (1954), 1899 ff to 1902, describe the amination of nonactivated olefins by means of an amine or $NH_3$ using alkali metals, alkali metal hydrides or alkali metal amides as catalysts. To achieve acceptable yields and conversions, it is necessary to employ temperatures of from about 175 to 200° C. and high pressures of above 400 atm. As the pressure is decreased, yield and conversion drop drastically.

Furthermore, processes which use highly sensitive and expensive catalysts, e.g. lanthanide compounds, and processes which are suitable only for the preparation of specific amines are known.

A broadly applicable method for the hydroamination of alkenes has therefore not been available hitherto.

It is an object of the present invention to provide an economical process for preparing alkylamines which makes do with readily available or easy-to-handle, inexpensive starting materials, makes it possible to obtain high space-time yields and selectivities and can be carried out over inexpensive catalyst systems.

The achievement of this object starts out from a process for preparing alkylamines (product amines) by reacting alkenes with amines (starting amines) in the presence of a metal hydride or metal as catalyst.

In the process of the present invention, the reaction is carried out in the presence of a cocatalyst whose acidity is higher than that of the starting amine.

The process of the present invention provides, for the first time, a single-stage route to amines from alkenes which has broad applicability and is carried out under conditions which are acceptable in industry. Inexpensive and readily available alkenes can be used as starting materials and, in addition, the lack of unavoidable by-products makes the reaction interesting from an ecological point of view. Use of the present process in the industrial production of amines thus leads to tremendous savings.

The alkenes used in the present process are preferably nonactivated alkenes. For the purposes of the present invention, nonactivated alkenes are alkenes whose olefinic double bond is not conjugated with other olefinic or aromatic double bonds or heteroatoms. The hydroamination of these alkenes is particularly difficult, since nucleophilic attack by the amine group on the olefinic double bond is not aided by activation of the double bond by conjugation or heteroatoms. However, alkenes obtained from nonactivated alkenes, e.g. ethene or propene, are of particular interest.

In principle, any nonactivated alkenes can be used in the process of the present invention. Preference is given to alkenes which do not bear any further functional groups. Particular preference is given to using nonactivated alkenes which contain from 2 to 20 carbon atoms and may be branched, unbranched or cyclic. Very particular preference is given to alkenes having from 2 to 6 carbon atoms, e.g., ethene, propene, n-butene having a double bond in position 1 or 2, isobutene, n-pentene having a double bond in position 1 or 2, isopentene and n-hexene having a double bond in position 1, 2 or 3 and also isohexene. Ethene and propene are very particularly preferably used.

The amines used (hereinafter referred to as starting amines) are alkylamines, alkylarylamines or arylamines such as aniline. Preference is given to primary or secondary alkylamines, particularly preferably secondary alkylamines. The alkyl group of the alkylamines can be branched, unbranched or cyclic. Preference is given to using alkylamines whose alkyl groups are saturated and which contain no functional groups. The alkyl groups particularly preferably have from 1 to 20 carbon atoms, very particularly preferably from 1 to 6 carbon atoms, i.e. the alkyl groups are very particularly preferably methyl, ethyl, n-/iso-propyl, n-/iso-/tert-butyl, n-pentyl or branched pentyl, n-hexyl or branched hexyl radicals. Very particular preference is given to using alkylamines whose alkyl radicals have from 1 to 4 carbon atoms. If secondary alkylamines are used, the alkyl groups of the alkylamines can be identical or different. Very particular preference is given to using ethylamine, diethylamine, isopropylamine, diisopropylamine and dimethylamine.

The alkylamines (or, if desired, alkylarylamines) prepared by the process of the present invention (hereinafter referred to as product amines) are preferably secondary or tertiary alkylamines (or, if desired, alkylarylamines). Depending on the amines used, the alkyl groups can be identical or different. Preferred alkyl radicals correspond to those of the amines used. Very particularly preferred examples of amines which can be prepared are triethylamine, diisopropylamine, ethylisopropylamine and ethyldimethylamine. These are preferably obtained by the reactions shown in the following table:

| Starting amine | Alkene | Product amine |
| --- | --- | --- |
| $H_2NEt$, $HNEt_2$ | Ethene | $NEt_3$, $HNEt_2$ |
| $H_2N^iPr$ | Propene | $HN(^iPr)_2$ |
| $HN(^iPr)_2$ | Ethene | $EtN(^iPr)_2$ |
| $HMe_2N$ | Ethene | $EtNMe_2$ |

Metal hydrides used in the process of the present invention are generally alkali metal hydrides such as lithium hydride, sodium hydride, potassium hydride, rubidium hydride and cesium hydride. Preference is given to using lithium hydride, sodium hydride, potassium hydride particularly preferably sodium hydride and potassium hydride and very particularly preferably sodium hydride. Preference is given to using hydrides which are in the form of pastes or suspensions in saturated hydrocarbons. Very particular preference is given to using pastes or suspensions of the hydrides in paraffin oil. The use of technical-grade hydrides as are marketed by the companies Callery, Chemmetall, Degussa-Hüls or Metallchemie is particularly preferred. These are pastes in saturated hydrocarbons packed in soluble polymer bags. They are generally contaminated by alkali metal and/or alkali metal hydroxide.

Metals used in the process of the present invention are generally alkali metals such as Li, Na, K, Rb or Cs, preferably Li, Na or K, particularly preferably Na or K, very particularly preferably Na.

It is also possible to use alloys of alkali metals with one another. Prepurification of the alkali metals before use in the reaction is not necessary. Thus, it is possible to use technical-grade alkali metal as is marketed, for example, by the companies Metaux-Speciaux, Chemmetall, Callery Chem. Comp., PA, or Alkali Metals Ltd., Hyderabad, India. The alkali metal is generally contaminated by hydroxides, oxides, alkaline earth metals, halides and, in the case of lithium, nitrides.

The hydrides and metals used as catalysts represent inexpensive, readily available and easy-to-handle catalysts which make it possible for the process of the present invention to be carried out cheaply, for a wide range of products and in an industrially practical manner.

Furthermore, preference is given to using hydrides which originate from the decomposition of alkali metal amides or organometallic compounds of alkali metals. The hydride can be formed in situ in the reactor, preferably at >50° C.

If hydrides which are in the form of a paste or suspension in saturated hydrocarbons are used, these hydrides can be used directly or can be washed to remove most of the paraffin oil before use in the process of the present invention. A person skilled in the art will be familiar with such washing procedures. In a preferred embodiment, the hydrides are freed of the saturated hydrocarbon by washing with the starting amine. Washing of the hydride used can be carried out directly in the reaction vessel or in another vessel with subsequent transfer.

It has been found that the reaction of alkenes with amines (starting amines) to form alkylamines (or, if desired, alkylarylamines) (product amines) which are preferably secondary or tertiary using metal hydrides or metals as catalysts proceeds in particularly high space-time yields when use is made of a cocatalyst whose acidity is higher than that of the amine. However, the acidity is preferably not so high and the nucleophilicity of the conjugate anion so low that addition onto ethylene becomes improbable. Without being tied to a theory, it is assumed that the acidity of the starting amines alone is not sufficient to make it possible for them to be quantitatively deprotonated by the metal hydride or metal used as catalyst, particularly when the hydrogen formed is not removed from the system. The cocatalyst can be deprotonated more readily by the metal hydride or metal used as catalyst and the metal complex obtained in this way is able to add onto the alkene. This results in formation of a metal-carbon bond which can easily be protonated by the starting amine, so that a metal complex of the metal of the metal hydride used and the starting amine is formed. This can then add onto the alkene used and continue the reaction cycle.

In a preferred embodiment, the cocatalyst used has an acidity of ≦35 on the McEven-Streitwieser-Appleguest-Dessy scale, preferably from 20 to 35, particularly preferably from 25 to 35, very particularly preferably from 30 to 35. The McEven-Streitwieser-Appleguest-Dessy scale is described in D. J. Cram, Fundamentals of Carbanion Chemistry 1965, Acad. Press, NY, chapter 1.

Preference is given to using unsaturated nitrogen compounds as cocatalysts. These can be imine compounds or the tautomeric enamine compounds. These can be cyclic or acyclic.

Preferred acyclic nitrogen compounds are selected from among acyclic imine compounds or the tautomeric enamine compounds of the formula (I) or (Ia)

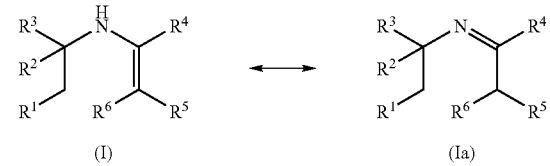

where the radicals $R^1$ to $R^6$ are, independently of one another, hydrogen or alkyl radicals which may be branched or unbranched and/or be interrupted by one or more nitrogen atoms. $R^1$ to $R^6$ are preferably $C_1$–$C_{20}$-alkyl radicals, particularly preferably $C_1$–$C_4$-alkyl radicals. Examples of suitable alkyl radicals are methyl, ethyl, n- and iso-propyl, n- and iso- and tert-butyl.

$R^1$ to $R^6$ can also, independently of one another, be cycloalkyl radicals which may be substituted by the above-mentioned functional groups or by alkyl, alkenyl or alkynyl groups and/or be interrupted by one or more nitrogen atoms. Preferred cycloalkyl radicals have from 3 to 12 carbon atoms, if desired partly replaced by nitrogen atoms, in their ring, particularly preferably 5 or 6 carbon atoms. The cycloalkyl radicals are very particularly preferably unsubstituted. Particularly useful cycloalkyl radicals are, for example, cyclopentyl and cyclohexyl.

Furthermore, the radicals $R^1$ to $R^6$ can also, independently of one another, be alkenyl radicals or alkynyl radicals which have one or more multiple bonds, preferably from 1 to 4 multiple bonds. The alkenyl or alkynyl radicals can, like the alkyl radicals, be substituted or interrupted by one or more nitrogen atoms.

It is also possible for two of the radicals $R^1$ to $R^6$ together to form a ring which may in turn be substituted by alkyl, alkenyl or alkynyl groups.

Particular preference is given to the radicals $R^1$ to $R^6$ being, independently of one another, hydrogen, methyl or ethyl, and very particular preference is given to each of the radicals $R^1$ to $R^6$ being hydrogen.

Suitable cyclic unsaturated nitrogen compounds include both cyclic enamines and N-heterocyclic compounds in the form of imines or enamines. Preferred cyclic enamines have a $C_4$–$C_8$ carbocyclic ring, particularly preferably a $C_4$–$C_6$ carbocyclic ring. This carbocyclic ring is at least monounsaturated and bears at least one amino group containing at least one hydrogen atom. Depending on the ring size, the carbocyclic ring may also have two or more double bonds. Preference is given to using cyclic enamines which are not conjugated further. The carbocyclic ring can be substituted by one or, depending on the ring size, more radicals apart from the amino group. Suitable radicals correspond to those mentioned above for $R^1$ to $R^6$ radicals, with the exception of hydrogen (in the discussion of the substitution of this carbocyclic ring by substituent radicals, a hydrogen atom is not counted as a substituent). Preferred radicals are alkyl radicals which may be branched or unbranched and have from 1 to 6, particularly preferably from 1 to 4, carbon atoms. The number of radicals is dependent on the ring size, with from zero to 3 radicals being preferred and the carbocyclic ring particularly preferably bearing no radical or one radical, very particularly preferably no radical.

Examples of suitable cyclic unsaturated nitrogen compounds are:

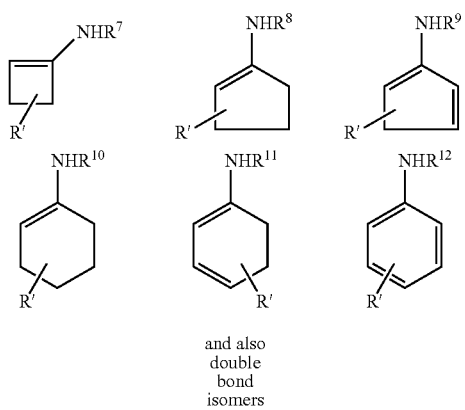

and also double bond isomers where $R^7$ to $R^{12}$ are each hydrogen or one of the radicals specified for $R^1$ to $R^6$. $R^7$ to $R^{12}$ are preferably hydrogen, methyl radicals or ethyl radicals, very particularly preferably hydrogen or ethyl radicals.

R' can represent one or more substituents on the carbocyclic ring, with the maximum number of radicals R' corresponding to the number of hydrogen atoms on the ring carbons. The number of radicals R' is preferably from 0 to 3, particularly preferably 0 or 1, very particularly preferably 0, i.e. all carbon atoms of the carbocyclic ring bear only hydrogen atoms with the exception of one carbon atoms which bears the amino group. Suitable radicals R' are alkyl radicals which may be branched or unbranched and/or may be interrupted by one or more nitrogen atoms. The radicals R' are preferably $C_1$–$C_{20}$-alkyl radicals, particularly preferably $C_1$–$C_4$-alkyl radicals. Examples of suitable alkyl radicals are methyl, ethyl, n- and iso-propyl, n- and iso- and tert-butyl.

The radicals R' can also, independently of one another, be cycloalkyl radicals which may be substituted by the abovementioned functional groups or by alkyl, alkenyl or alkynyl groups and/or be interrupted by one or more nitrogen atoms. Preferred cycloalkyl radicals have from 3 to 12 carbon atoms, some of which may be replaced by nitrogen atoms, in their ring, particularly preferably 5 to 6 carbon atoms. The cycloalkyl radicals are very particularly preferably unsubstituted. Particularly useful cycloalkyl radicals are, for example, cyclopentyl and cyclohexyl.

Furthermore, the radicals R' can, independently of one another, also be alkenyl radicals or alkynyl radicals which have one or more multiple bonds, preferably from 1 to 4 multiple bonds. The alkenyl or alkynyl radicals may, like the alkyl radicals, be substituted or interrupted by one or more nitrogen atoms.

It is also possible for two of the radicals R' together to form a ring which may in turn be substituted by alkyl, alkenyl or alkynyl groups.

The radicals R' are particularly preferably, independently of one another, methyl, ethyl or n- or iso-propyl.

Among the compounds mentioned, very particular preference is given to enamines which are not conjugated further and are selected from among

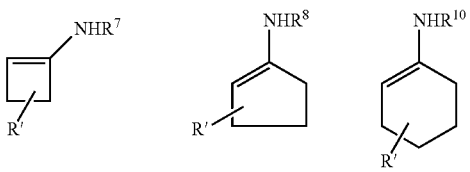

As N-heterocyclic compounds in the form of imines or enamines, preference is given to using cyclic compounds having a total of from 3 to 20 atoms, preferably from 5 to 12 atoms, particularly preferably from 5 to 7 atoms. The N-heterocyclic compound may contain further heteroatoms, preferably nitrogen atoms, in addition to the nitrogen atom which is necessarily present. The number of further heteroatoms depends on the ring size. N-Heterocyclic compounds having a ring size of 5 or more atoms preferably contain from zero to 2 further heteroatoms, particularly preferably no further heteroatom or 1 further heteroatom. The carbon atoms of the N-heterocyclic compound may bear further radicals. Suitable radicals are the same as those which have been mentioned above as radicals R' on the carbocyclic rings of the abovementioned cyclic enamines. In the case of N-heterocyclic compounds which contain further heteroatoms, preferably nitrogen atoms, in addition to the N atom, not only the carbon atoms but also the heteroatoms except for one nitrogen atom may bear further radicals R'. Apart from the imine or enamine double bond, the N-heterocyclic compounds may contain further double bonds which may be conjugated or not conjugated with the imine or enamine double bond. Preference is given to using N-heterocyclic compounds which have no conjugated double bonds.

Examples of suitable N-heterocyclic compounds are:

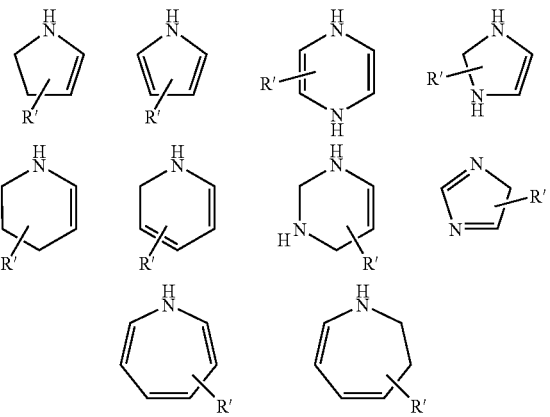

Here, the radical R' is defined as for the radical R' in the preferred cyclic enamines described above. The number of substituents R' is preferably 0 to the number of ring atoms minus 1; particular preference is given to all ring atoms of the N-heterocyclic compounds bearing hydrogen atoms or a radical R', with at least one nitrogen atom of the N-heterocyclic ring bearing a hydrogen atom.

Among the abovementioned compounds, particular preference is given to N-heterocyclic compounds which have no conjugated double bonds and are selected from among

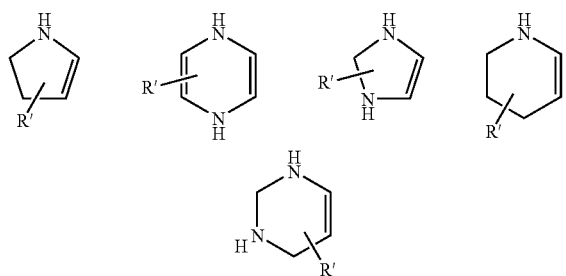

Very particular preference is given to compounds of the following formula:

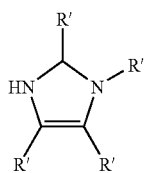

where R' is as defined above.

In particular, the cocatalyst is an imine or tautomeric enamine compound which is formed in the dehydrogenation of the starting and/or product amines or a decomposition or reaction product of the appropriate imine or tautomeric enamine compound. The cocatalyst is very particularly preferably an imine or tautomeric enamine compound which is formed in the dehydrogenation of the starting amine or a decomposition or reaction product of the imine or tautomeric enamine compound.

The desired cocatalyst can be prepared and added separately to the starting materials. However, it is also possible to prepare the cocatalyst in situ before or during the reaction (hydroamination reaction). In a preferred embodiment, the cocatalyst is formed by reacting the hydride or metal used as catalyst with the monoalkylamine or dialkylamine (or, if desired, monoarylamine or diarylamine or alkylarylamine) chosen as starting amine prior to the reaction with the alkene and removing the hydrogen formed from the reaction mixture. It is preferably distilled and subsequently separated into a gas phase, a low-boiling fraction comprising the starting amine and the cocatalyst and a bottom fraction comprising the hydride or the metal. The low-boiling fraction is subsequently added to the bottom fraction, the procedure described is repeated if appropriate and the hydroamination is started by addition of alkene and, if appropriate, further starting amine.

It is also possible for the desired cocatalyst to be formed during the reaction. The formation of the cocatalyst during the reaction is preferably brought about by reacting the starting amines with alkenes in the presence of a metal hydride or metal as catalyst, with the reaction mixture obtained preferably being fractionally distilled to give a gas phase (a) comprising hydrogen and unreacted alkene, a low-boiling fraction (b) comprising unreacted starting amine and the cocatalyst, a middle fraction (c) comprising the product amine and a bottom fraction (d) comprising the catalyst. The fraction (b) is supplemented with fresh starting amine and alkene and combined with the bottom fraction comprising the catalyst. It is also possible to isolate the unreacted alkene from the gas phase (a) and recirculate it together with the low-boiling fraction (b) to the bottom fraction.

In a preferred embodiment, the process of the present invention is carried out with hydrogen formed during the reaction being removed from the reaction mixture. This is preferably brought about by distillation or stripping. It has to be ensured that the residual materials separated off in the distillation are returned, wholly or partly, to the process.

Without being tied to a theory, a possible mechanism leading to the formation of the cocatalyst in the in-situ formation of the cocatalyst prior to the reaction with the alkene is described below using the reaction of sodium hydride and diethylamine as an example. The proposed mechanism applies equally to the use of metal hydrides and the use of metals as catalysts.

The reaction of sodium hydride with diethylamine leads to the formation of small amounts of NaNEt$_2$. This probably decomposes according to the following scheme:

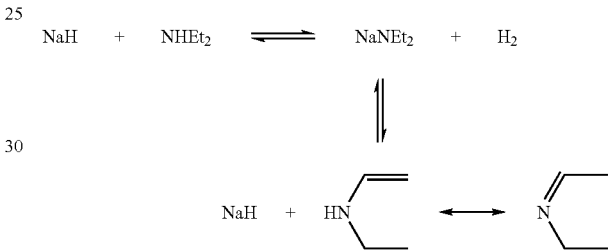

The enamine/imine formed has sufficient acidity to bring about protonation of the sodium hydride or oxidation of the metal to a high degree.

As an alternative or in addition, the imine can also be formed by dehydrogenation of the starting amine in the presence of a hydrogenation/dehydrogenation catalyst, which is shown below for the example of diethylamine as starting amine:

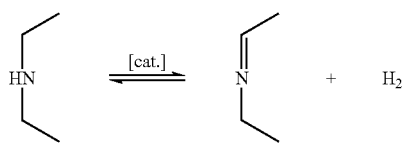

[cat.]=hydrogenation/dehydrogenation catalyst

Suitable hydrogenation/dehydrogenation catalysts are all customary hydrogenation/dehydrogenation catalysts. Use is generally made of transition metal catalysts in the form of all-active or supported catalysts. Preferred transition metals are selected from the groups VIIIb and Ib of the Periodic Table of the Elements. Particular preference is given to Fe, Ru, Co, Ni, Pd, Pt and Cu or alloys of these metals. Suitable support materials are, for example, carbon, SiO$_2$, Al$_2$O$_3$, ZrO$_2$ and TiO$_2$. The hydrogenation/dehydrogenation catalysts may further comprise promoters/modifiers selected from among Sn, Sb, alkali metals, alkaline earth metals, Bi and Pb. Examples of suitable hydrogenation/dehydrogenation catalysts are Raney Ni, Raney Cu, Raney Co, Pd/γ-Al$_2$O$_3$, Pt/carbon, Ru/SiO$_2$, Pd/Sn/Cs/γ-Al$_2$O$_3$.

The precise compositions of suitable hydrogenation/dehydrogenation catalysts are known to those skilled in the art.

In a preferred embodiment of the process of the present invention, the hydrogenation/dehydrogenation catalysts are introduced into a reactor together with the metal hydride or metal used as catalyst.

In another preferred embodiment of the process of the present invention, the hydrogen is removed from the system during the above-described reactions so as to shift the equilibrium further in the direction of the desired cocatalysts.

The present invention therefore also provides a process according to the invention for preparing alkylamines (product amines) by reacting alkenes with amines (starting amines) in the presence of a metal hydride or metal as catalyst, in which the reaction is carried out in the presence of a cocatalyst and which comprises the following steps:

reaction of the metal hydride or metal with the starting amine in the presence or absence of a hydrogenation/dehydrogenation catalyst, separation of a gas phase (a) comprising hydrogen and a low-boiling fraction (b) comprising the cocatalyst and starting amine from a bottom fraction (c) comprising the metal hydride or the metal, preferably by distillation, recirculation of the low-boiling fraction (b) to the bottom fraction (c), if appropriate, repetition of the above steps, reaction to the desired product amines by addition of alkene and, if appropriate, further starting amine.

In this process, the formation of the cocatalyst occurs in situ prior to the reaction of the starting amine with the alkene (hydroamination). It is also possible for the formation of the cocatalyst to occur during the reaction of the starting amine with the alkene.

The formation of the cocatalyst in situ during the hydroamination is preferably part of a process for preparing alkylamines (product amines) by reacting alkenes with amines (starting amines) in the presence of a metal hydride or metal as catalyst, in which the reaction is carried out in the presence of a cocatalyst and which comprises the following steps:

reaction of the alkenes with the starting amines in the presence of the metal hydride or metal as catalyst, in the presence or absence of a hydrogenation/dehydrogenation catalyst, fractionation of the reaction mixture, preferably by distillation, to give a gas phase (a) comprising hydrogen and unreacted alkene, a low-boiling fraction (b) comprising the cocatalyst and starting amine, a middle fraction (b) comprising the desired alkylamine (product amine) and a bottom fraction (c) comprising the metal hydride or metal, recirculation of the low-boiling fraction (b) to the bottom fraction (c), addition of fresh alkene and starting amine and if appropriate, separation of the gas phase (a) into hydrogen and alkene and recirculation of the alkene together with the low-boiling fraction (b).

This procedure can be carried out a number of times during the course of the reaction to provide fresh cocatalyst for the reaction. Furthermore, it is possible to conceive of a combination in which the cocatalyst is firstly formed in situ prior to the reaction, without addition of the alkene, and further cocatalyst is subsequently formed in situ in the presence of the alkene during the reaction.

The process of the present invention can be carried out continuously, batchwise or semicontinuously (e.g. by metered addition of alkene). The order in which the starting materials are added can generally be chosen without restriction and the addition can be carried out either simultaneously or successively. In a preferred embodiment, the cocatalyst is formed during the hydroamination (reaction of the alkenes with amines (starting amines) in the presence of a metal hydride or metal as catalyst).

In general, the reaction is carried out at from 50 to 200° C., preferably from 70 to 150° C., particularly preferably from 90 to 130° C. The reaction pressure is generally from 3 to 300 bar, preferably from 10 to 100 bar, particularly preferably from 20 to 60 bar. This means that neither particularly high pressures nor particularly high temperatures which could require particular safety precautions are necessary for carrying out the process of the present invention. The reaction time (residence time) is dependent on the starting materials used and on the desired degree of conversion. It is generally from 0.2 to 20 hours, preferably from 0.3 to 10 hours, particularly preferably from 0.3 to 10 hours.

Suitable apparatuses for carrying out the process of the present invention can be, depending on whether the process is continuous, batchwise or semicontinuous, various reactor types such as bubble columns (preferably cascaded), stirred vessels into which gas is introduced or jet loop reactors or combinations of these reactors.

The alkali metal compound formed from alkali metal or alkali metal hydride and the cocatalyst can be present as a homogeneous solution in the liquid phase or, when its solubility is exceeded, in suspension together with the metal or hydride.

To prevent the formation of deposits of alkali metal, alkali metal hydrides and/or alkali metal salts, preference is given to using stirred vessels or cascades of stirred vessels with appropriate agitators.

When the process is carried out batchwise, the addition products formed (hydroamination products) are preferably distilled from the reactor. The catalyst can, as long as it still has sufficient activity, remain in the reactor and can thus be utilized for further reactions.

When the process is carried out continuously, the adduct formed can be separated off from the reaction mixture by, for example, stripping with unreacted alkenes. However, the reaction mixture is preferably taken in liquid form from the reactor and passed to flash evaporation or distillation. As an alternative to a thermal work-up of the reaction mixture with subsequent recirculation of the catalyst, it is possible to use, for example, a filtration for recirculating or holding back the catalyst.

The molar ratio of starting amine to the alkene used is generally from 20:1 to 1:10, preferably from 10:1 to 1:5, particularly preferably from 2:1 to 1:2.

The metal hydride or metal (catalyst) is generally used in an amount of from 0.01 to 30 mol %, preferably from 0.1 to 10 mol %, particularly preferably from 1 to 3 mol %, based on the amine used. The cocatalyst is generally present in an amount of from 0.002 to 2 mol %, preferably from 0.02 to 1 mol %, particularly preferably from 0.05 to 0.5 mol %, based on the amine used.

Secondary and tertiary amines can be prepared in space-time yields of generally from 1 to 5000 kg/m$^3$h, preferably from 10 to 1000 kg/m$^3$h, particularly preferably from 50 to 200 kg/m$^3$h, by means of the process of the present invention. The yield of the desired amines is, depending on the time, generally from 20 to 100%, preferably from 50 to 95%, particularly preferably from 70 to 90%, based on the amine used.

Suitable solvents for the hydroamination are:
a) hydrocarbons, preferably saturated hydrocarbons having from 2 to 100 carbon atoms. Particular preference is given to paraffin oil, n-butane, i-butane, n-pentane, i-pentane, n-hexane, i-hexane and cyclohexane.
b) tertiary amines, preferably trialkylamines, with the alkyl groups of the trialkylamines very particularly preferably having from 1 to 10 carbon atoms. Both linear and branched alkyl groups and also cycloalkyl groups are suitable.

Very particular preference is given to using the desired tertiary product amine as solvent.

In the batchwise embodiment of the process of the present invention, the dried starting amines (e.g. dried over molecular sieves) are introduced together with a metal hydride, preferably sodium hydride or potassium hydride, or a metal, preferably sodium or potassium, into a pressure vessel. The reaction mixture is subsequently heated to the desired temperature and the total pressure is set by metered addition of the appropriate gaseous alkene. After a reaction time of from 0.5 to 20 hours, preferably from 1 to 10 hours, particularly preferably from 2 to 4 hours, the gaseous substances (hydrogen and unreacted alkene) and the low boilers (cocatalyst and any unreacted starting amine) are partly separated off by distillation. The low boilers and any unreacted alkene are returned to the reaction mixture and the hydroamination reaction is continued. After a further reaction time of from 0.1 to 20 hours, preferably from 0.5 to 10 hours, particularly preferably from 1 to 4 hours, the distillation/recycle procedure is repeated if necessary. The hydroamination reaction is then continued, if appropriate with addition of fresh starting amine and fresh alkene. If desired, the distillation/recycle procedure can be repeated another one or more times.

The product amine can be obtained in the respective distillation procedures and/or after work-up of the total contents of the reactor.

In the very particularly preferred continuous embodiment of the process of the present invention, the reaction product mixture comprising from 5 to 60% by weight of starting amine, from 30 to 95% by weight of product amine, from 0.1 to 20% by weight of alkene and from 0.1 to 10% by weight of metal hydride or metal and also from 0.01 to 1% by weight of cocatalyst is fed into a flash vessel. The pressure in the flash vessel is preferably selected so that temperatures of from 100 to 150° C. result in the flash vessel.

The liquid output from the flash vessel, which comprises from 60 to 98.79% by weight of product amine, from 1 to 30% by weight of starting amine, from 0.2 to 30% by weight of metal hydride or metal and from 0.01 to 0.2% by weight of cocatalyst is recirculated to the reactor. The product amine obtained in this liquid output is continuously discharged.

Most of the output from the reactor is taken off from the flash vessel in vapor form and is subsequently passed to work-up by distillation.

The low boilers obtained at the top of the column in the work-up by distillation, which comprise the starting amine, the cocatalyst, the alkene and hydrogen, are, except for the hydrogen, recirculated to the reactor.

In this method of carrying out the process, the cocatalyst is formed predominantly in the flash vessel, since hydrogen and cocatalyst are continuously taken from the equilibrium between starting amine and metal hydride or metal on one side and hydrogen and cocatalyst on the other side.

The flash vessel thus represents a "cocatalyst reactor". This function of the flash vessel can also be taken over by the bottom of a column to which the output from the reactor is fed directly. The column pressure is preferably set so that the temperature at the bottom is from 100 to 150° C.

A hydrogenation/dehydrogenation catalyst can additionally be present in the flash vessel or in the bottom of the column.

The present invention further provides for the use of a cocatalyst in the preparation of alkylamines (product amines) by reacting alkenes with amines (starting amines) in the presence of a metal hydride or metal as catalyst, where the cocatalyst has an acidity which enables it to protonate the metal hydride or oxidize the metal more readily than the amine itself. Preferred embodiments of the cocatalyst, the metal hydride or metal and of the alkenes and starting amines are indicated above.

The following examples illustrate the invention.

EXAMPLES

The starting amines were dried over 3 Å molecular sieves and introduced together with commercial NaH or KH (suspension in paraffin oil, washed with diethylamine) into a 0.11 steel autoclave. The autoclave was then heated to 120° C. (NaH) or 100° C. (KH) and a total pressure of 50 bar (NaH) or 45 bar (KH) was set by injection of ethylene. To follow the reaction, samples were taken from the liquid phase via a valve, analyzed by gas chromatography (30 m RTX-5 amine) and the results were converted into percent by mass using empirically determined correction factors.

The Comparative Experiments 1 to 3 which are presented first are reactions of diethylamine with ethylene in the presence of sodium hydride or potassium hydride as catalyst in the absence of a cocatalyst.

Comparative Experiment 1

Reaction of 70 g of Diethylamine With Ethylene Over 3 g of NaH

| Time [h] | Yield of triethylamine | Yield per unit time [1/h] |
|---|---|---|
| 3 | 7% | 2% |
| 4.5 | 12% | 3% |
| 6 | 19% | 5% |
| 7 | 24% | 5% |
| 8 | 31% | 7% |
| 9 | 36% | 5% |
| 10 | 40% | 5% |
| 11 | 43% | 3% |
| 12 | 47% | 4% |
| 13 | 50% | 3% |

Comparative Experiment 2

Reaction of 70 g of diethylamine with ethylene over 3 g of NaH with the low boilers being distilled off (mass of condensate: 35 g; composition: 0.6% of ethene, 0.15% of imine (N-ethylideneethylimine), 92.46% of diethylamine, 6.61% of triethylamine) and replaced by diethylamine after a time of 1 hour and with the procedure being repeated (mass of condensate: 35 g; composition: 0.61% of ethene, 0.11% of imine (N-ethylideneethylimine), 85.65% of diethylamine, 13.29% of triethylamine) after a total time of 3 hours.

| Time [h] | Yield of triethylamine | Yield per unit time [1/h] |
|---|---|---|
| 1 | 4% | 4% |
| 2 | 8% | 4% |
| 3 | 13% | 5% |
| 4 | 19% | 6% |
| 5.75 | 27% | 5% |
| 6.5 | 31% | 6% |

Comparative Experiment 3

Reaction of 70 g of Diethylamine With Ethylene Over 3 g of KH

| Time [h] | Yield of triethylamine | Yield per unit time [1/h] |
|---|---|---|
| 1 | 1% | 1% |
| 2 | 5% | 4% |
| 3 | 12% | 7% |
| 4 | 19% | 8% |
| 5 | 28% | 8% |
| 6 | 38% | 10% |
| 7 | 44% | 6% |
| 8 | 50% | 7% |
| 8.75 | 55% | 6% |

Experiment 1

Reation of 70 g of diethylamine with ethylene over 3 g of NaH with the low boilers being distilled off (mass of condensate: 35 g; composition: 0.22% of ethene, 0.13% of imine (N-ethylideneethylimine), 95.59% of diethylamine, 3.92% of triethylamine) and recycled after a time of 1 hour and with the procedure being repeated (mass of condensate: 35 g; composition: 0.2% of ethene, 0.17% of imine (N-ethylideneethylimine), 70.41% of diethylamine, 29.01% of triethylamine) after a total time of 3 hours.

| Time [h] | Yield of triethylamine | Yield per unit time [1/h] | Comment |
|---|---|---|---|
| 1 | 3% | 3% | |
| 2 | 16% | 14% | High activity due to recycling |
| 3 | 25% | 9% | |
| 4.2 | 42% | 15% | High activity due to recycling |
| 5 | 50% | 10% | |
| 6 | 57% | 7% | |

Experiment 2

Reaction of 70 g of diethylamine with ethylene over 3 g of KH with the low boilers being distilled off (mass of condensate: 35 g; composition: 0.45% of ethene, 0.06% of imine (N-ethylideneethylimine), 77.88% of diethylamine, 21.41% of triethylamine) and recycled to the beginning of the experiment.

| Time [h] | Yield of triethylamine | Yield per unit time [1/h] | Comment |
|---|---|---|---|
| 1 | 7% | 7% | High activity due to recycling |
| 2.17 | 17% | 9% | |
| 3 | 24% | 8% | |

Experiment 3

Reaction of 68.5 g of diethylamine and 1.5 g of N-ethylideneethylimine with ethylene over 3 g of NaH with the low boilers being distilled off (mass of condensate: 35 g; composition: 0.2% of ethene, 0.02% of imine (N-ethylideneethylimine), 80.15% of diethylamine, 19.41% of triethylamine) and recycled after a time of 1 hour.

| Time [h] | Yield of triethylamine | Yield per unit time [1/h] | Comment |
|---|---|---|---|
| 1 | 13% | 13% | High activity due to imine |
| 2 | 29% | 16% | High activity due to recycling |

It can be clearly seen that the activity of the alkali metal hydride is increased after the low boilers have been distilled off and the distillate has been returned to the reaction. The reaction finally slows again due to deactivation of the catalyst and can be accelerated again by once again distilling off the low boilers and returning them to the reaction. Alternatively, the high activity of the alkali metal hydride is obtained at the beginning of the experiment when a few percent by weight of N-ethyleneethylimine are added to the diethylamine as cocatalyst.

It can be concluded from this that, without being tied to a theory, the distillation and recycling results in decomposition of diethylamine into N-ethylideneethylimine and $H_2$ and in removal of the $H_2$ formed from the system. This hypothesis is supported by the following experiment:

Experiment 4

Pretreatment of 70 g of diethylamine and 3 g of NaH with 50 bar of $H_2$ at 120° C., followed by cooling, depressurization, injection of 50 bar of ethylene and reaction with ethylene at 120° C.

| Time [h] | Yield of triethylamine | Yield per unit time [1/h] |
|---|---|---|
| 3 | 0.3% | 0.1% |
| 6 | 0.7% | 0.1% |
| 10 | 1.1% | 0.1% |
| 13 | 1.4% | 0.1% |

We claim:
1. A process for preparing alkylamines (product amines) by reacting alkenes with primary or secondary alkylamines (starting amines) in the presence of a metal hydride or metal as catalyst, wherein the reaction is carried out in the presence of a cocatalyst which is an unsaturated nitrogen compound.

2. A process as claimed in claim 1, wherein the alkenes are nonactivated alkenes whose olefinic double bond is not conjugated with other olefinic or aromatic double bonds or hetero forms.

3. A process as claimed in claims 1, wherein the amines prepared (product amines) are secondary or tertiary alkylamines.

4. A process as claimed in claim 1, wherein the cocatalyst is an imine or tautomeric enamine compound which is formed by dehydrogenation of the amine used (starting amine).

5. A process as claimed in claim 4, wherein the cocatalyst is formed in situ before or during the reaction of the starting amine with the alkene.

6. A process as claimed in claim 1, wherein the reaction is carried out at from 50 to 200° C.

7. A process as claimed claim 1, wherein the pressure during the reaction is from 2 to 300 bar.

8. A process for preparing alkylamines (product amines) by reacting alkenes with amines (starting amines) in the presence of a metal hydride or metal as catalyst, wherein the reaction is carried out in the presence of a cocatalyst which is an unsaturated nitrogen compound, selected from the group consisting of acrylic imine compounds or the tautomeric enamine compounds of the formula I or Ia

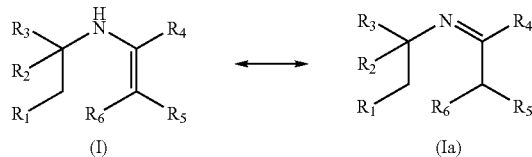

and where the the radicals $R^1$ to $R^6$ are, independently of one another, hydrogen or alkyl radicals which may be branched or unbranched and/or be interrupted by one or more nitrogen atoms, $R^1$ to $R^6$ can also, independently of one another, be cycloalkyl radicals which may be substituted by the abovementioned functional groups or by alkyl, alkenyl or alkynyl groups ad/or be interrupted by one or more nitrogen atoms furthermore, the radicals $R^1$ to $R^6$ can also, independently of one another, be alkenyl radicals or alkynyl radicals which have one or more multiple bonds it is also possible for two of the radicals $R^1$ to $R^6$ together to form a ring which may in turn be substituted by alkyl, alkenyl or alkynyl groups, cyclic unsaturated nitrogen compounds of the following formulas

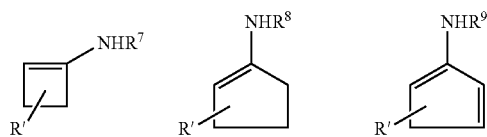

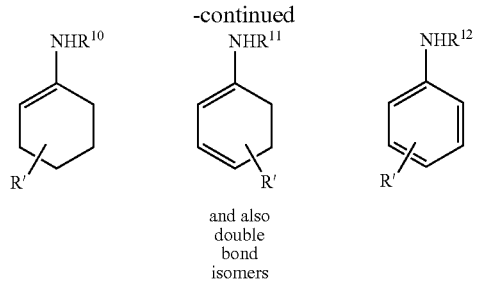

and also double bond isomers and where $R^7$ to $R^{12}$ are each hydrogen or one of the radicals specified for $R^1$ to $R^6$ R' can represent one or more substituents on the carboxylic ring, with the maximum number of radicals R' corresponding to the number of hydrogen atoms on the ring carbons, suitable radicals R' are alkyl radicals which may be branched or unbranched and/or may be interrupted by one or more nitrogen atoms, the radicals R' can also, independently of one another, be cycloalkyl radicals which may be substituted by the abovementioned functional groups by alkyl, alkenyl or alkynyl groups and/or be interrupted by one or more nitrogen atoms, furthermore, the radicals R' can, independently of one another, also be alkenyl radicals or alkynyl radicals which have one or more multiple bonds, it is also possible for two of the radical R' together to form a ring which may in turn be substituted by alkyl, alkenyl, or alkynyl groups, and N-heterocyclic compounds of the following formulae

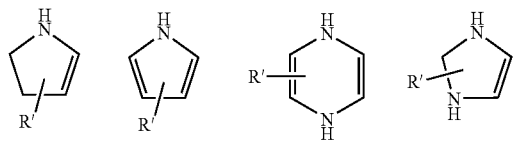

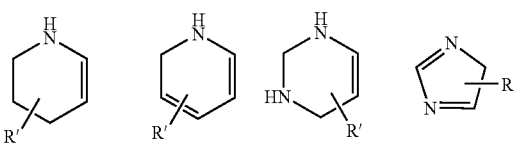

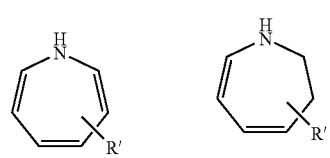

wherein the radical R' is defined as for the radical W in the cyclic enamines described above, the number of substituents R' is 0 to the number of ring atoms minus 1.

9. A process as claimed in claim 8, wherein the alkenes are nonactivated alkenes whose olefinic double bond is not conjugated with other olefinic or aromatic double bonds or hetero forms.

10. A process as claimed in claim 8, wherein the amines used (starting amines) are primary or secondary alkylamines.

11. A process as claimed in claims 8, wherein the mines prepared (product amines) are secondary or tertiary alkylamines.

12. A process as claimed in claim 8, wherein the cocatalyst is an brine or tautomeric enamine compound which is formed by dehydrogenation of the amine used (starting amine).

13. A process as claimed in claim 12, wherein the cocatalyst is formed in situ before or during the reaction of the starting amine with the alkene.

14. A process as claimed in claim 8, wherein the reaction is carried out at from 50 to 200° C.

15. A process as claimed claim 8, wherein the pressure during the reaction is from 2 to 300 bar.

* * * * *